United States Patent [19]

Zardi

[11] 4,210,600
[45] Jul. 1, 1980

[54] METHOD FOR THE PREPARATION OF UREA WITH A HIGH-YIELD REACTOR

[75] Inventor: Umberto Zardi, San Donato Milanese, Italy

[73] Assignee: Snamprogetti, S.p.A., Milan, Italy

[21] Appl. No.: 40,863

[22] Filed: May 21, 1979

Related U.S. Application Data

[63] Continuation of Ser. No. 845,371, Oct. 25, 1977, abandoned.

[30] Foreign Application Priority Data

Oct. 28, 1976 [IT] Italy .............................. 28779 A/76

[51] Int. Cl.² ........................................... C07C 126/02
[52] U.S. Cl. ................................................ 260/555 A
[58] Field of Search ..................................... 260/555 A

[56] References Cited

U.S. PATENT DOCUMENTS

| | | | |
|---|---|---|---|
| 3,105,093 | 9/1963 | Rothkrans | 260/555 A |
| 3,446,601 | 5/1969 | Heunks | 260/555 A |
| 3,957,868 | 5/1976 | Verstegen | 260/555 A |

*Primary Examiner*—Brian E. Hearn
*Attorney, Agent, or Firm*—Morgan, Finnegan, Pine, Foley & Lee

[57] ABSTRACT

In a total recycle urea-producing system, the improvement is disclosed which consists in providing in the reactor two adjoining but separated reaction spaces, called first and second reaction zones, the surface which separates the two zones being a heat-exchanging surface. Fresh ammonia and carbon dioxide are fed with a portion of excess recycled ammonia to the first reaction zone, wherein the reaction is exothermic in character, whereas the condensates from the carbamate decomposition and the remaining portion of the excess recycled ammonia are fed to the second reaction zone, wherein the reactions are of an endothermic nature. By so doing, a better thermal balance in the reactor is obtained, concurrently with improved yields.

3 Claims, 3 Drawing Figures

METHOD FOR THE PREPARATION OF UREA WITH A HIGH-YIELD REACTOR

This is a continuation of application Ser. No. 845,371, filed Oct. 25, 1977, now abandoned.

This invention relates to a method for the production of urea employing a high-yield reactor.

Urea is usually produced by synthesis from $NH_3$ and $CO_2$ in reactors which are operated at a high pressure and a high temperature. The reaction is not a complete one, and only a portion of the reactants is converted into urea.

In up-to-date installations, all the unconverted reactants are usually recycled to the reactor (total recycle process) so as to achieve a complete conversion of $NH_3$ and $CO_2$, through a number of methods which involve various procedures. The best known methods for the total recycle of unreated components provide for the recycle of the entire unconverted $CO_2$ and of part of the unconverted $NH_3$ to the reactor in the form of an aqueous solution of ammonium carbamate and a discrete recycle of the remaining $NH_3$ in a pure state. The most recent of the so-called stripping methods provides for the recycle of the major fraction of the unreacted $CO_2$ in an isobaric loop which includes the reactor and the decomposer (stripper). Conversely, ammonia is recycled in the form of aqueous solutions of ammonium carbonate, and partly in the pure condition. In the earlier urea installations, only a part of the reactants was converted into urea ("once-through", or partial recycle method) and no recycle of the unconverted reactants, or a partial recycle only, was carried out in the reactor.

In all the recycling methods (either partial or total), the reactor is fed with the fresh reactants coming from the installation ($NH_3+CO_2$) which are intimately admixed with the recycled aqueous solutions of ammonium carbamate and/or carbonate which contain an excess of $NH_3$, and with the excess of recycled ammonia.

The reactor is usually of the adiabatic type in the total recycle installations: the feeds (fresh reactants plus recycled solutions and recycled excess ammonia) are intimately admixed, and the heat evolved by the sum of the following reactions raises the temperature of the reactants to the desired value:

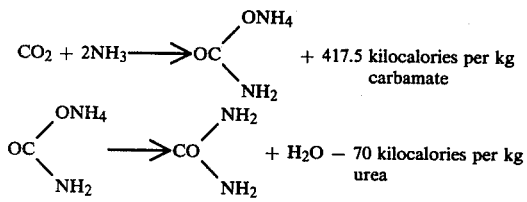

The reactor is not thermally balanced in the "once-through" and "partial recycle" methods wherein the excess heat is removed, usually for producing steam.

The yield of conversion into urea of $NH_3$ and $CO_2$ in the reactor is improved by the temperature and by high molar ratios of $NH_3$ to $CO_2$, and is impaired by the presence of $H_2O$. The pressure in the interior of the reactor is maintained at a sufficiently high value in order to ensure that the maximum amount of the reactants is in the liquid phase (as a matter of fact, the reactions must take place in the liquid phase). The vapor pressure of the reaction solution (reactor melt) is increased as the temperature is increased and as the molar ratio $NH_3$ to $CO_2$ is increased, and is decreased as the contents of $H_2O$ is increased. The maximum working temperature of the reactor is determined by corrosion and urea decomposition problems.

As a rule, the temperature of 220° C. is never exceeded, that would which impose the use of high-corrosion-resistant materials for the inner reactor lining (e.g. titanium, zirconium). Such materials are extremely expensive and pose technological problems in the construction of the reactors, especially when high working pressures are required.

In the temperature range of from 190° C. to 220° C. it is required, in order that all the reactants be maintained in the liquid phase, that very high pressures are adopted, over 190 kilograms/sq.cm, and this requirement involves a high power consumption, especially for the compression of $CO_2$.

In the stripping processes, the reactor pressure is optimized with the decomposer (stripper) pressure in an isobaric loop. The pressure within the reactor thus does not exceed 155 kgs/sq.cm.

As a result, the maximum molar ratio $NH_3$ to $CO_2$ which can be obtained while still maintaining the reactants in the liquid phase is from 3.0 to 3.5 at a maximum temperature of 185°–190° C.

There are, consequently, limitations on the yield, which does not exceed, as a rule, 60% ($CO_2$ yield).

In the conventional methods (nonstripping) with total recycle the following are the usual working conditions for the reactor:

Pressure: 200 to 400 kilograms/sq.cm
Temperature: 190° to 220° C.
Molar ratio $NH_3$ to $CO_2$(N/C): 3.6 to 5.0
Molar ratio $H_2$ to $CO_2$ (H/C): 0.5 to 1.0
$CO_2$ yields: 60% to 80%

The method which employs the high-yield reactor, the subject-matter of the present invention, makes it possible for high yields to be obtained, even when working under comparatively low pressures and temperatures, thus doing away with the drawbacks of the high power consumptions, the high costs due to the use of expensive materials and of the technological problems set forth hereinabove. This method makes it possible, in addition, to work, in the stripping procedures, at a low pressure within the stripper in order to encourage the carbamate decomposition, while concurrently obtaining high yields in the reactor.

The method according to the present invention comprises the step of feeding fresh ammonia and carbon dioxide (stoichiometrically) together with a fraction of excess, recycle ammonia to a first reaction zone which is separated by heat-exchanging surfaces from a second reaction zone placed within the reactor and to which are fed the condensates obtained by decomposition of the ammonium carbamate, together with the remaining fraction of the excess, recycle ammonia.

The two zones can be operated under the same pressure in the range of from 100 to 250 atmospheres (abs.) or under different pressures, the high pressure being in the first reaction zone with respect to the second one, the pressure of the first zone being susceptible of exceeding that of the second zone, even by as much as 200 atmospheres (abs.).

In the first reaction zone there is a strong heat excess relative to the heat which would be required to maintain the appropriate reaction temperature. In the heat-deficient second zone, the lacking heat is supplied at the expense of the heat evolved in the first zone, through a heat-exchange separation surface.

The second zone, to which is fed the carbamate and/or carbonate solution and a portion of the excess recycle $NH_3$, there can be fed, if necessary, a small fraction of $CO_2$, not exceeding 10%, in order to obtain the optimum ratios of $NH_3$ to $CO_2$, and $H_2O/CO_2$ and to adjust the heat balance.

It is important to observe that, in the method according to the present invention, the ratio of ammonia to carbon dioxide in the two discrete reaction zones of the high-yield reactor must be so Adjusted as to have a ratio of 2.5 to 5 in the first zone, to which is fed fresh reactants and a portion of the excess recycle ammonia, and must be from 3.5 to 8 in the second zone to which are fed the recycle carbamate and/or carbonate together with the remaining portion of the excess recycle ammonia.

The solution of urea, coming from the first and second zones of the reactor which are operated under the same pressure or under a pressure gradient (from 0 to 200 kgs/sq.cm) between the two zones, the higher pressure being in the first zone, feeds the downstream treatment section for the recycle of the unconverted reactants.

The reactor having two reaction zones operated under different pressures is especially useful in the stripping procedures, wherein the stripping of the solution coming from the reactor and the recycle of the carbamate are effected in the low-pressure zone of the reactor under the same pressure, a high yield in the reactor being thus obtained while concurrently achieving a high degree of decomposition of the carbamate in the stripper.

BRIEF DESCRIPTION OF THE DRAWING

FIG. 1 of the accompanying drawings illustrates an embodiment of the present invention in the case of a method for the production of urea wherein the stripping of the urea solution emerging from the reactor is carried out. Obviously, this is but a nonlimiting exemplary and particular illustration.

Figure 1:
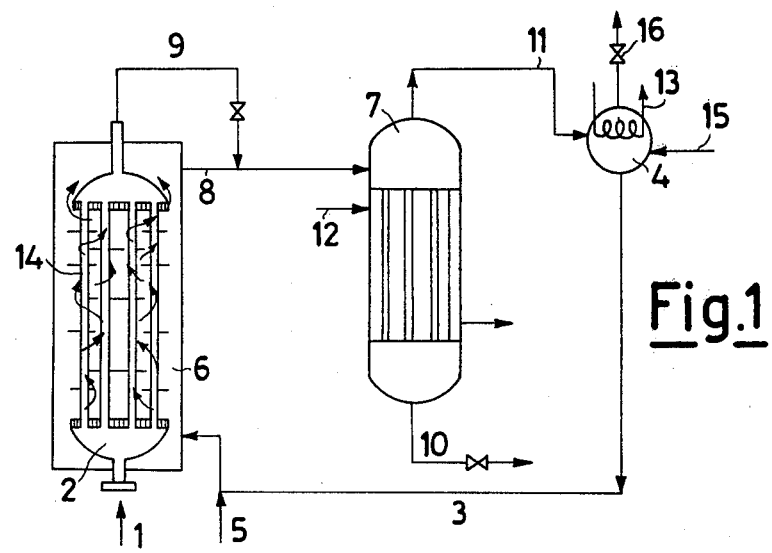
FIG. 1 is a schematic illustration of apparatus adapted for use in the practice of my invention when the pressure in the first reaction zone is higher than the pressure in the second reaction zone.

The fresh reactants ($NH_3+CO_2$), indicated at 1, are fed to the reaction zone 2, which is operated under the higher pressure. The solution of recycle carbamate 3, coming from the carbamate condenser 4, together with a portion of the feed $NH_3$, 5, are fed to the reaction zone 6, which is operated under the same pressure as the isobaric loop which includes the carbamate decomposer, or stripper 7, and the carbamate condenser 4, The solution of urea 8, which contains carbamate and residual $NH_3$, coming from the reaction zone 6, and the solution of urea 9, coming from the higher-pressure zone 2, are fed to the stripper 7 which is operated under the same pressure as the reaction zone 6.

The solution of urea 10, virtually devoid of carbamate and having a small residual content of ammonia, emerging from the bottom of the decomposer or stripper 7, feeds the downstream treatment sections.

The vapors 11, of $NH_3+CO_2+H_2O$, coming from the top of stripper 7 are fed to the carbamate condenser 4.

The heat required by stripper 7 for decomposing the carbamate and evaporating off $NH_3$ and $H_2O$ is supplied by steam 12.

The heat evolved at 4 by the condensation of the vapors $NH_3+CO_2+H_2O$ and the carbamate reforming, is removed to produce steam 13.

The reaction zone 6 and the apparatuses 4 and 7 work unde the same pressure of about 160 kgs/sq.cm. The reaction zone 2, is operated under a higher pressure, say 220 kgs/sq.cm. The excess heat evolved by the zone 2 is supplied to the zone 6 which requires heat, through the exchange surface 14.

Figure 2:
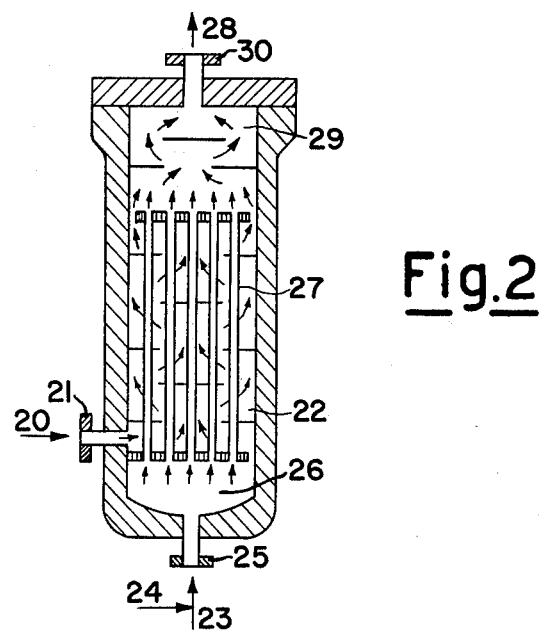
FIG. 2 is a schematic illustration of a modified reactor adapted for use in the practice of my invention when the first and second reaction zones are maintained at the same pressure.

This invention will now be further illustrated by the embodiment shown in FIG. 2, which obviously is but another exemplary and nonlimiting embodiment.

With reference now to FIG. 2, a methd is described in which a reactor is used wherein the two reaction zones are under the same pressure.

The fresh reactants $NH_3+CO_2$, 20, are fed through the nozzle 21 to the first reaction zone 22. The carbamate solution 23, and a portion of the fresh ammonia 24, are fed through the nozzle 25 to the second reaction zone 26. Through the heatexchange surfaces 27 the excess heat from the first reaction zone 22 is transferred to the second reaction zone 26, which requires heat.

The urea solution 28, coming from the two zones 22 and 26 which feed the mixing zone 29 and emerges through the nozzle 30.

A few examples will now be given in order that the invention be still better illustrated without limiting the scope thereof.

EXAMPLE 1

Yield in the reactor: 80%.

With reference to FIG. 1, there are the following two reaction zones:

| 1st reaction zone: Feed, at 1 | | |
|---|---|---|
| $NH_3$ | 1274 kgs. | N/C = 4.5 |
| $CO_2$ | 733 kgs. | H/C = 0 |
| Total | 2007 kgs. | |

Reaction conditions: Temperature 190° C., pressure 220 atm.

Yield=83% (obtained experimentally according to Mavrovic and Otsuka-Inoue-Jojima).

Outlet from first reaction zone, 2: $NH_3$=804 kgs.; $CO_2$: 124 kgs.; Urea: 830 kgs.; $H_2O$: 249 kgs. Totalling 2007 kgs.

Stream 3, emerging from the second reaction zone 6: $NH_3$=247 kgs.; $CO_2$: 180 kgs.; $H_2O$: 89 kgs.; totalling 516 kgs.

Stream 5: $NH_3$: 103 kgs.

Combined streams 5 and 3: $NH_3$=350 kgs.; $CO_2$=180 kgs.; $H_2O$=89 kgs., totalling 619 kgs.

The N/C ratio is 5 and the H/C ratio is 1.2.

Reaction conditions: Temperature: 185° C.; pressure 160 atm.

Yield: 69% (experimental data according to Mavrovic and Otuska-Jojima).

Outlet from the second reaction zone 6: $NH_3 = 254$ kgs. $CO_2 = 56$ kgs.; Urea = 170 kgs.; $H_2O = 140$ kgs. for a total of 620 kgs.

Summing up, if the streams 8 and 9 emerging from the two reaction zones are combined together, the following is the rate of flow which is obtained:

$NH_3 = 57$ kgs.; $CO_2 = 180$ kgs.; Urea 1,000 kgs.; $H_2O = 389$ kgs, total 2626 kgs.

The N/C ratio is 4.6, the H/C ratio is 0.24 and the yield is 80%.

In order to obtain the same yield according to OTSUKA, Inoue,Jojima (171st ACS National Meeting, 1976) the following working conditions ought to be adopted:

N/C ration = 5; Temperature = 215° C.; Pressure = 421 atm.

The streams 8 and 9 are fed to the stripper 7, thus obtaining as a bottom stream 10: $NH_3 = 280$ kgs.; $CO_2 = 30$ kgs.; Urea = 1,000 kgs.; water = 350 kgs, and as a top stream 7: $NH_3 = 808$ kgs.; $CO_2 = 150$ kgs.; water = 39 kgs.

The decomposition at 7 is obtained working at 160 atm and 215° C. on the bottom stream 10.

All the $CO_2$ and $H_2O$ and a portion of $NH_3$ coming from 7 are condensed at 4 (Pressure = 160 atm; temperature 185° C.), to which is fed, in addition, the stream 15 formed by solutions of carbonate coming from the downstream treatment sections of the urea solutions. The heat evolved at 4 is used for the production of steam 13, at a pressure of 8 atm. The uncondensed ammonia together with the inerts introduced with $CO_2$ are discharged into the downstream sections by the vent 16.

EXAMPLE 2

Yield in the reactor: 72%.

With reference to FIG. 2, there are the following two reaction zones:

1st reaction zone 22: Feed 20 through nozzle 2.

$NH_3 = 907$ kgs.: $CO_2 = 733$ kgs, totalling 1640 kgs. N/C = 3.2; H/C = 0: Reaction conditions: temperature 190° C.: pressure = 180 atm. Yield = 74% (experimental data according to the calculation after Mavrovic and Otsuka-Inoue-Jojima). Outlet from the 1st reaction zone 22:

$NH_3 = 487$ kgs.:$CO_2 = 191$ kgs.; Urea: 740 kgs.: $H_2O = 222$ kgs.: for a total of 1640 kgs.

2nd reaction zone 26: feeds 23 and 24, nozzle 25.

Stream 23 (carbamate recycle):

$NH_3 = 377$ kgs.; $CO_2 = 276$ kgs. $H_2O$: 135 kgs, totalling 788 kgs. Stream 24, of $NH_3$: 155 kgs of $NH_3$. Combined stream 23 and 24.

$NH_3 = 533$ kgs.; $CO_2$: 276 kgs.; $H_2O = 135$ kgs, for a total of 944 kgs. N/C = 5; H/C = 1.2.

Reaction conditions: temperature = 185° C.; pressure = 180 atm.

Yield = 69% (experimental data calculated according to Navrovic and Otsuka-Inoue-Jojima).

Outlet from the second reaction zone 26:

$NH_3 = 386$ kgs.; $CO_2 = 85$ kgs.; Urea = 260 kgs.; $H_2O = 213$ kgs, for a total of 944 kgs.

The stream 28, obtained by combining the streams emerging from the two reaction zones has the following composition:

$NH_3 = 873$ kgs.; $CO_2 = 276$ kgs.: Urea = 1,000 kgs.; $H_2O = 435$ kgs, totalling 2584 kgs. N/C is 3.7, H/C is 0.33 and the yield is 72%.

In order to obtain the same yield, according to Otsuka-Inoue-Jojima (171st ACS National Meeting, 1976) it is required that the following working conditions be adopted:

According to a further, improved aspect of the present invention, a procedure is available for obtaining optimum $NH_3$ to $CO_2$ molar ratios in the two reaction zones aforementioned.

To achieve this improved result, it is possible to work under such conditions that a portion of the excess ammonia is separated at the outlet of the first reaction zone and recycled directly to said first zone.

As regards the thermal balance of the reactor, it is possible, in order to maintain it, to remove heat from the first reaction zone for producing steam, or by the agency of a coolant.

Figure 3:
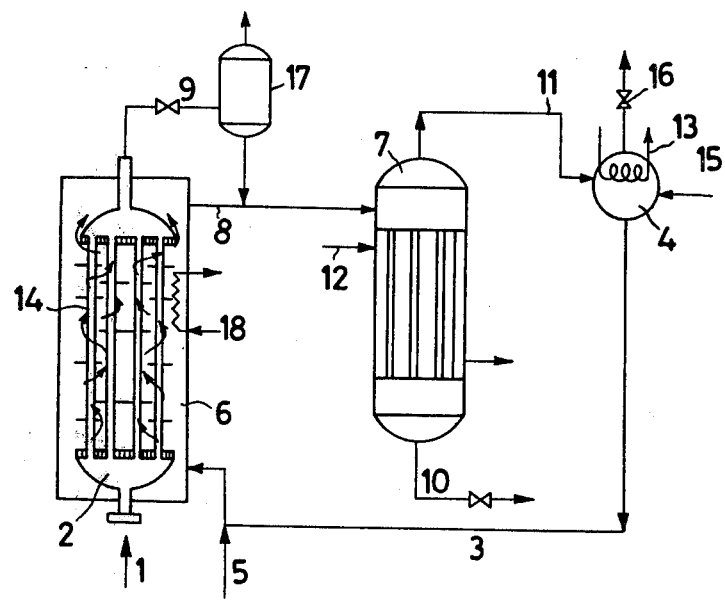
FIG. 3 is a schematic illustration of a modification of the apparatus illustrated schematically in FIG. 1.

The accompanying FIG. 3 is a nonlimiting illustration of this quite particular aspect of the present invention.

in FIG. 3, the numerals of component parts illustrated in FIG. 1 hereof have been retained and have the same meanings: thus, the description of component parts already described in connection with FIG. 1 will not be repeated.

As regards the portions of FIG. 3 which do not appear in FIG. 1, it can be said that the solution of urea 9, is sent to the separator 17 from which emerges, at the top, a portion of the excess ammonia, which is recycled towards 1, the excess heat of the reaction zone 6, being removed by a cooling coil 18.

I claim:

1. The method of producing urea with a high-yield reactor having a first reaction zone, a second reaction zone and a heat exchange surface separating said first reaction zone from said second reaction zone and operated at elevated temperatures and at sufficient pressures to maintain the reactants in the liquid phase, the pressure in the first reaction zone being in the range between the pressure in the second reaction zone and 200 atmospheres above said second reaction zone pressure, which includes the steps of:
    (a) synthesizing a quantity of urea by feeding to said first reaction zone a stoichiometric mixture of $NH_3$ and $CO_2$ together with a portion of excess recycle $NH_3$ sufficient to provide an $NH_3/CO_2$ ratio in the range of from 2.5 to 5 in said first reaction zone feed so that an exothermic reaction generating heat in excess of the amount required to synthesize said quantity of urea is carried out in said first reaction zone;
    (b) synthesizing a further quantity of urea through an endothermic reaction by feeding to said second reaction zone ammonium carbamate condensate together with the balance of said excess recycle $NH_3$ to provide an $NH_3/CO_2$ ratio in the range of 3.5 to 8 and withdrawing from the first reaction zone to the second reaction zone through said heat exchange surface sufficient heat to maintain the endothermic reaction in the second reaction zone;
    (c) withdrawing from said reactor a stream containing an aqueous solution of urea, ammonium carbamate, and excess recycle $NH_3$;
    (d) separating urea from the stream withdrawn through step (c);
    (e) withdrawing excess recycle $NH_3$ from the stream withdrawn through step (c);
    (f) supplying a portion of the excess recycle $NH_3$ withdrawn through step (e) to the feed for the first reaction zone in step (a);

(g) forming ammonium carbamate condensate from said ammonium carbamate; and (h) supplying said ammonium carbamate condensate and the balance of the excess recycle $NH_3$ withdrawn through step (e) to the feed for the second reaction zone in step (b).

2. The method of producing urea as claimed in claim 1, wherein the pressure in said first reaction zone is in the range of from 100 to 250 absolute atmospheres.

3. The method of producing urea as claimed in claim 1, wherein said stream withdrawn from the reactor comprises a first zone output stream emerging from the first reaction zone and a second zone output stream emerging from the second reaction zone, and wherein a portion of said excess recycle $NH_3$ supplied to the first reaction zone is separated from said first zone output stream and is recycled directly to said first reaction zone.

* * * * *